United States Patent [19]

Kawamata et al.

[11] Patent Number: 4,533,552
[45] Date of Patent: Aug. 6, 1985
:::

[54] STABILIZATION OF AZULENE DERIVATIVES

[75] Inventors: Masanobu Kawamata; Koichi Ushimaru, both of Kyoto; Hiroyuki Goshi, Shiga; Hideichi Miyasako, Moriyama, all of Japan

[73] Assignee: Nippon Shinyaku Co., Ltd., Japan

[21] Appl. No.: 473,452

[22] Filed: May 11, 1983

[30] Foreign Application Priority Data

Mar. 9, 1982 [JP] Japan ................................. 57-37411

[51] Int. Cl.[3] .................. C07C 143/24; A61K 31/185
[52] U.S. Cl. ................................. 424/78; 260/505 R; 260/505 P; 424/80; 424/81; 514/553; 514/970
[58] Field of Search ............... 260/503, 505 R, 505 P; 424/315

[56] References Cited

FOREIGN PATENT DOCUMENTS 1034327 12/1958 Fed. Rep. of Germany .
49-11219 3/1974 Japan .
0108012 7/1982 Japan ................................. 424/315

OTHER PUBLICATIONS

Weissberger, Separation & Purification Part I, vol. III, (1956), pp. 821–822.
Perry, Perry's Chem. Eng. Handbook, 4th ed., (1963), pp. 20–59.

*Primary Examiner*—Alan Siegel
*Attorney, Agent, or Firm*—Jacobs & Jacobs

[57] ABSTRACT

Sodium 1,4-dimethylisopropylazulene-3-sulfonate is stabilized by adding to a solution thereof, physiologically non-toxic additives and then removing or separating the solvent therefrom by spray drying or a lyophilization.

13 Claims, No Drawings

STABILIZATION OF AZULENE DERIVATIVES

The present invention relates to a method of stabilizing sodium 1,4-dimethylisopropylazulene-3-sulfonate which is a water-soluble derivative of guaiazulene.

Sodium 1,4-dimethylisopropylazulene-3-sulfonate (abbreviated hereinafter as GASN) exhibits anti-inflammatory and anti-ulcer activity and has been widely used in the form of tablets and granules. Though GASN is soluble in warm water, alcohol and acetic anhydride, it is sparingly soluble in cold water and is nearly insoluble in ether and benzene. Therefore it is usually purified by recrystallization from water. When recrystallized from water, the resulting crystals are needles or flakes.

GASN is an unstable compound in its solid form and, even at room temperature, it decomposes.

Thus, even if it is made into pharmaceutical preparations such as tablets or granules, storage for a long time is not possible. Several attempts at stabilizing GASN have been reported such as adding anti-oxidants and weakly basic metal salts or alkali earth metal salts to make GASN stable against heating (cf. German Pat. No. 1,034,327) or more recently, adding an amino acid (cf. Japanese patent publication No. Sho-49-11219). However, the resulting effects are not always sufficient to stabilize GASN.

The stabilizing method according to the present invention comprises dissolving GASN in a suitable solvent and rapidly removing the solvent by the method which is described below.

Thus, GASN is dissolved in water, lower aliphatic alcohols or an aqueous solution of such alcohols and then the solvent is rapidly removed therefrom by spray-drying or by lyophylization. Examples of suitable lower aliphatic alcohols are straight or branched chain alcohols with one to four carbon atoms and the use of methyl alcohol or ethyl alcohol is preferred. There will be no particular restriction in the concentration of alcohol when such alcohols are used as aqueous solutions.

One of the most important aspects of the present invention is the method of removing the solvent. Both spray-drying and lyophylization which have never been thought of as means for stabilization are particularly suitable for the removal of the solvent whereupon a solute which is heat stable is obtained.

By evaporation of the solvent under ordinary pressure or in vacuo using such an apparatus as rotary evaporators, the solution is concentrated and a part of solute is obtained as crystals but, in such methods, there is no hope of obtaining stabilized solute. Removal of the solvent rapidly by spray-drying or by lyophilization is required.

Powder X-ray diffraction of the GASN obtained according to the present invention does not show, as compared with that of crystalline form, any particular peak and therefore it is obvious that the produce is non-crystalline. This is a very characteristic aspect of the GASN produce obtained by the present invention.

The following non-limitative examples more particularly illustrate the present invention.

EXAMPLE 1

GASN (50 grams) is dissolved in 5 liters of water of 25° C. and subjected to a spray-drying with 2 liters per hour of air (air intake temperature: 100° C.) using a mobile minor type spray drier (Niro Company) to give finely powdered GASN.

EXAMPLE 2

GASN (50 grams) is dissolved in 5 liters of water of 25° C. Lactose (4950 grams) is subjected to a flowing with air whose in-taking temperature is 70° C. using a grain manufacturing apparatus WSG-5 (Gratt-Okawara) and the above obtained solution is sprayed thereupon at the rate of 100 ml/minute followed by drying to give a composition containing 1% of GASN.

EXAMPLE 3

GASN (50 grams) is dissolved in 3.5 liters of 50% methanol at room temperatures and, by the similar way as in Example 2 (air in-take temperature: 60° C.) to give a composition in which the ratio of GASN:lactose is 1:99.

EXAMPLE 4

GASN (1 gram) is dissolved in 100 ml of water and subjected to lyophilization by a lyophilizer (DC-35) (Yamato) using acetone-dry ice as a freezing mixture.

The GASN prepared in Examples 1 to 4 is made into samples as described below, allowed to stand at 40° C., and the residual GASN is measured by the following expression.

$$\text{Amount of GASN (mg)} = \frac{A}{20.25} \times 1000$$

by observing the extiction at 568 nm in a phospate buffer of pH 7.0. Data concerning stability after stored at 40° C. are given in Table 1.

Methods of preparing samples are as follows:
Sample 1: GASN (1 gram) prepared by Example 1 is mixed with 99 grams of lactose to make 100 grams.
Sample 2: Composition prepared by Example 2 is used as it is.
Sample 3: Composition prepared by Example 3 is used as it is.
Sample 4: GASN (1 gram) prepared by Example 4 is mixed with 99 grams of lactose to make 100 grams.
Control: GASN untreated (1 gram) is mixed with 99 grams of lactose to make 100 grams.

Each sample is placed in Petri dishes and the upper surface is tightly closed with polyethylene film. The quantitative value immediately after manufacture is set 100.

TABLE 1

| | Residual Rate (%) of GASN kept at 40° C. | | | | |
|---|---|---|---|---|---|
| Sample | Immediately after Manuf. | 1 Week | 2 Weeks | 3 Weeks | 4 Weeks later |
| 1 | 100 | 97.9 | 91.4 | 80.3 | 68.6 |
| 2 | 100 | 98.9 | 97.1 | 94.1 | 92.6 |
| 3 | 100 | 97.8 | 95.3 | 93.4 | 90.4 |
| 4 | 100 | 98.1 | 79.6 | 54.1 | 28.7 |
| Control | 100 | 26.3 | 3.5 | 0 | 0 |

Table 1 shows that the GASN obtained by a method of the present invention is highly stable as compared with the control.

In the above methods, addition of inert or active soluble additives to a GASN solution followed by similar treatment will not destroy the stability of GASN so long as the above-given procedure for rapid removal of the solvent is followed. It is noted that stability of GASN in the composition to which insoluble additives is added is nearly the same as those of compositions of Examples 2 and 3.

Another characteristic feature of the present invention is that, prior to removal of the solvent, soluble or insoluble additives are added thereto. Such additives include sugars, macrogols, surface active agents, inorganic or organic salts and the like whereby there is almost no change in the stability of GASN as compared with the compositions of Examples 2 and 3. However, when polymers (which themselves are used as viscosity-increasing agents, dispersing agents, or combining agents for tablets or granules) are added to a solution together with GASN and the solution is subjected to drying by spray-drying or by lyophilization, the resulting compositions exhibit markedly increased stability as compared with the compositions which do not contain such polymers. This result is quite a novel and unexpected one.

Suitable polymers are compounds generally used as viscosity-increasing agents, dispersing agents or combining agents. Representative examples of them are vinyl type polymers (such as polyvinyl pyrrolidone, polyvinyl alcohol, etc.), acryl type polymers (such as sodium polyacrylate, etc.), cellulose derivatives (such as methyl cellulose, ethyl cellulose, Carbohole 934®, hydroxypropyl cellulose, hydroxypropyl methyl cellulose, carboxymethyl cellulose, etc.), starches separated from plant materials (such as corn, potato, rice, wheat, tapioca, Japanese arrowroot, etc.), processed starches (such as heat-treated starch, oxidized starch, acid-treated starch, oxygen-treated starch, alpha-starch, etc.), starch derivatives (such as starch phosphate sodium, carboxymethyl starch, etc.), and natural materials (such as tragacanth, sodium alginate, gelatin, agar-agar, etc.).

The amount of polymer to be added should be 0.5% or more by weight. There will be no stabilizing effect when 0.5% or less is added to GASN. When 0.5% or more amount is added, there is a marked increase in stabilizing effect as compared with GASN compositions of Examples 2 and 3. Of course, mixtures of such polymers may be used. Other soluble or insoluble additives may also be added to the GASN solution.

The powder X-ray diffraction pattern of GASN prepared by the method of the present invention or of the composition containing such GASN does not show a strong diffraction peak which is recognized as indicating needles or flakes obtained by recrystallizing GASN from water and it is a characteristic of the present invention that the product is non-crystalline. Non-crystalline substances are generally unstable from a thermodynamic viewpoint as compared with crystalline ones and, accordingly, their stability will be lower. However, quite surprisingly, in this case the non-crystalline GASN is very stable. This is quite unexpected and there is no other similar example so far as we know.

Further examples of the present invention are as follows. The stability of GASN in the composition is given in Table 2.

EXAMPLE 5

GASN (10 grams) and 90 grams of polyvinylpyrrolidone (Plasdon C which is a Registered Trademark) are dissolved in 1 liter of water and subjected to a spray-drying using mobole minor spray-drier (Niro Company) under the condition of intake air temperature 120° C. and spraying liquid volume 40 ml/minute whereupon a composition containing 10% GASN is obtained.

EXAMPLE 6

GASN (20 grams) and 100 grams of polyvinyl alcohol (Gosenol-Registered Trademark) are dissolved in 2 liters of water. Lactose (4880 grams) is made fluidized in a mobilized layer grain-manufacturing apparatus WSG-t (Gratt-Okawara) under the condition of air intake temperature of 70° C. and the GASN-polyvinyl alcohol solution is sprayed thereupon at 100 ml/minute and dried to give a composition containing 0.4% GASN.

EXAMPLE 7

GASN (50 grams) and 100 grams of hydroxypropyl cellulose (HPC-L which is a Registered Trademark) are dissolved in 2 liters of methanol. Lactose (4850 grams) is made fluidized in the same apparatus as used in Example 6 under the condition of air intake temperature of 60° C. and the above solution is sprayed thereupon at 150 ml/minute to give a composition containing 1% GASN.

EXAMPLE 8

Potato starch (20 grams) is dissolved in 1 liter of hot water, the solution is allowed to stand at room temperatures, 10 grams of GASN is dissolved therein, and treated the same as in Example 6 using 4970 grams of lactose to give a composition containing 0.1% GASN.

EXAMPLE 9

GASN (1 gram) and 9 grams of carboxymethyl cellulose sodium (Cellogen 7A, Registered Trademark) are dissolved in 200 ml of water, subjected to a lyophilization using acetone-dry ice mixture, and a composition containing 20% of GASN is obtained.

Stability data of the compositions prepared by Examples 5 to 9 stored at 40° C. are shown in Table 2.
Sample 5: The composition of Example 5
Sample 6: The composition of Example 6
Sample 7: The composition of Example 7
Sample 8: The composition of Example 8
Sample 9: The composition of Example 9
Control: The composition prepared by a mere mixing of 1 gram of GASN with 5 grams of PVA and 94 grams of lactose Mere mixtures of the compositions of samples 5, 7, 8 and 9 in the same mixing ratio show the similar results and, accordingly, the above composition is selected as a representative control.

TABLE 2

| | Residual GASN (%) after stored at 40° C. | | | | | | | |
|---|---|---|---|---|---|---|---|---|
| | Immediately after Manuf | 2 Wks | 1 | 2 | 3 | 4 | 5 | 6 months later |
| Sample 5 | 100 | 100.8 | 99.5 | 99.2 | 98.8 | 99.3 | 98.1 | 96.3 |
| Sample 6 | 100 | 99.6 | 99.6 | 99.0 | 99.8 | 98.9 | 98.3 | 97.5 |
| Sample 7 | 100 | 99.1 | 99.4 | 98.9 | 99.5 | 98.6 | 99.0 | 98.4 |
| Sample 8 | 100 | 99.8 | 99.0 | 99.5 | 99.1 | 98.7 | 98.8 | 97.9 |
| Sample 9 | 100 | 100.3 | 99.8 | 98.9 | 97.3 | 96.0 | 95.1 | 93.2 |

TABLE 2-continued

| | Residual GASN (%) after stored at 40° C. | | | | | | |
|---|---|---|---|---|---|---|---|
| | Immediately after Manuf | 2 Wks | 1 | 2 | 3 | 4 | 5 | 6 months later |
| Control | 100 | 29.6 | 0 | — | — | — | — | — |

Table 2 shows that GASN in the compositions of Examples 5 to 9 is very stable and, even when stored at 40° C. for six months, hardly any decomposition is observed. Residual GASN in Samples 5 to 9 is 99–100% after one month and, when compared with the residual rate (28–92%) of the samples without additives (Samples 1–4 in Table 1) after four weeks, it is apparent that they are very stable.

Thus, a method of treating GASN after addition of a viscosity increasing agent showed marked effect as compared with a method of treating GASN without such additives. Such a method can be easily incorporated into manufacturing steps of pharmaceutical preparations and the compositions prepared thereby can be offered as pharmaceuticals in a form of powder of fine grains as they are or may be applied as granules for the manufacture of tablets and capsules.

What is claimed is:

1. A composition containing sodium 1,4-dimethylisopropylazulene-3-sulfonate and a stabilizing amount of a suitable polymer.

2. A composition according to claim 1 wherein the polymer is a viscosity-increasing agent, a dispersing agent or a combining agent.

3. A composition according to claim 1 wherein the polymer is a vinyl polymer, an acryl polymer, a cellulose derivative, a starch separated from plant material, a process starch, a starch derivative, tragacanth, sodium alginate, gelatin or agar-agar.

4. A composition according to claim 1 wherein the stabilizing amount is at least 0.5%.

5. A method of stabilizing sodium 1,4-dimethylisopropylazulene-3-sulfonate against heat which comprises dissolving sodium 1,4-dimethylisopropylazulene-3-sulfonate in a suitable solvent, adding a physiologically non-toxic stabilizing amount of a suitable polymer and removing the solvent from the solution by spray-drying or lyophilization.

6. A method according to claim 5 wherein the solvent is water, a lower aliphatic alcohol or an aqueous solution of a lower aliphatic alcohol.

7. A method according to claim 5 wherein the solvent is water.

8. A method according to claim 5 wherein the solvent is a lower aliphatic alcohol.

9. A method according to claim 8 wherein the lower aliphatic alcohol is a straight or branched chain alcohol of 1–4 carbon atoms.

10. A method according to claim 9 wherein the alcohol is methyl alcohol or ethyl alcohol.

11. A method according to claim 5 wherein the additive is a viscosity-increasing agent, a dispersing agent or a combining agent.

12. A method according to claim 5 wherein the polymer is a vinyl polymer, an acryl polymer, a cellulose derivative, a starch separated from plant material, a process starch, a starch derivative, tragacanth, sodium alginate, gelatin or agar-agar.

13. A method according to claim 5 wherein at least 0.5% of the polymer is added.

* * * * *